(12) United States Patent
Nelson

(10) Patent No.: US 7,862,836 B2
(45) Date of Patent: Jan. 4, 2011

(54) PHOSPHORUS BINDER FOR TREATMENT OF KIDNEY DISEASE

(75) Inventor: Deanna Jean Nelson, Cary, NC (US)

(73) Assignee: Biolink Life Sciences, Inc., Cary, NC (US)

( * ) Notice: Subject to any disclaimer, the term of this patent is extended or adjusted under 35 U.S.C. 154(b) by 881 days.

(21) Appl. No.: 11/402,545

(22) Filed: Apr. 12, 2006

(65) Prior Publication Data

US 2006/0228424 A1    Oct. 12, 2006

Related U.S. Application Data

(60) Provisional application No. 60/670,492, filed on Apr. 12, 2005.

(51) Int. Cl.
*A61K 33/34* (2006.01)
*A61K 33/06* (2006.01)
*A61K 31/385* (2006.01)
*A61K 31/19* (2006.01)

(52) U.S. Cl. .................. 424/617; 424/682; 514/54; 514/440; 514/574; 514/557

(58) Field of Classification Search ............. 424/617, 424/682; 514/54, 440, 574, 557
See application file for complete search history.

(56) References Cited

U.S. PATENT DOCUMENTS 6,187,780 B1 * 2/2001 Blech et al. ............ 514/252.16

FOREIGN PATENT DOCUMENTS

WO    WO 03094933 A2 * 11/2003

OTHER PUBLICATIONS http://mysite.du.edu/jcalvert/phys/phosphor.htm, Mar. 15, 2008.*

* cited by examiner

*Primary Examiner*—Ardin Marschel
*Assistant Examiner*—Zohreh Vakili
(74) *Attorney, Agent, or Firm*—Casimir Jones, SC

(57) ABSTRACT

The present invention relates to oral compositions which are useful for binding phosphorus in ingesta, and inhibiting absorption of phosphorus from the gastrointestinal tract of subjects. A method for binding phosphorus in ingesta and inhibiting its absorption from the gastrointestinal tract is also provided. The dietary supplements and pharmaceutical products and methods of the present invention are particularly useful in the treatment of hyperphosphatemia of chronic uremia and reducing serum phosphorus levels in patients requiring such therapy.

7 Claims, No Drawings

PHOSPHORUS BINDER FOR TREATMENT OF KIDNEY DISEASE

CROSS-REFERENCE TO RELATED APPLICATIONS

This application is related to provisional patent application Ser. No. 60/670,492, filed on 12 Apr. 2005, to which I claim priority.

STATEMENT REGARDING FEDERALLY SPONSORED RESEARCH & DEVELOPMENT

No Federally sponsored research & development were used in making this invention.

FIELD OF THE INVENTION

The present invention relates to oral compositions which are useful for binding phosphorus in ingesta, and inhibiting absorption of phosphorus from the gastrointestinal tract. A method for binding phosphorus in ingesta and inhibiting its absorption from the gastrointestinal tract is also provided. The dietary supplements and pharmaceutical products and methods of the present invention are particularly useful in the treatment of hyperphosphatemia of chronic uremia and reducing serum phosphorus levels in subjects requiring such therapy.

BACKGROUND OF THE INVENTION

Phosphorus, the sixth most abundant element in the human body, is critical for bone mineralization, cellular structure, genetic coding, and energy metabolism. Approximately 1,000 g of phosphorus, constituent in a variety of organic and inorganic forms, is present in an adult human. About 80-90% of the phosphorus is in bone, 10-14% is intracellular, and the remaining 1% is extracellular.

Phosphorus is present in nearly all foods, and absorption of dietary phosphorus from ingesta in the gastrointestinal (GI) tract is very efficient. Normal daily dietary intake varies from 800-1,500 mg of phosphorus. Typically, 70-90% of dietary phosphorus is absorbed, primarily from the jejunum, duodenum, and proximal ileum of the GI tract, although some absorption continues throughout the remainder of the intestinal tract. A small amount of GI excretion occurs.

In the normal adult human, serum phosphorus levels range from 2.5 to 4.5 mg/dL (0.81 to 1.45 mmol phosphorus/L). (Normal serum levels are typically 50% higher in infants and 30% higher in children due to growth hormone effects.) A condition of phosphorus homeostasis is normally maintained in the body of a subject, wherein the amount of phosphorus absorbed from the gastrointestinal tract approximately equals the amount excreted via the kidney. In addition, cellular release of phosphorus is balanced by uptake in other tissues. Hormonal control is provided by parathyroid hormone.

Since the kidney plays a central role in maintaining phosphorus homeostasis, kidney dysfunction is often accompanied by increased phosphorus retention by the body. In early kidney dysfunction, compensatory physiological responses allow for a continued match between urinary phosphorus excretion and phosphorus absorption from the gastrointestinal (GI) tract. With more advanced renal failure, however, elevated serum phosphorus is a predictable co-morbidity.

Hyperphosphatemia is a disease state in which there is an abnormally elevated serum phosphorus (Pi) level in the body. Hyperphosphatemia is a particular problem of chronic kidney disease (CKD) patients who are treated using dialysis. Conventional dialysis fails to reduce levels of phosphorus in the blood, and serum phosphorus levels increase with time. Significant hyperphosphatemia is considered present when serum phosphorus levels are greater than about 5 mg/dL in adults or 7 mg/dL in children or adolescents. [National Kidney Foundation. Am J Kidney Dis 2003; 42 (Suppl 3):S1-S201.]

In patients with CKD, phosphorus retention (as evidenced by abnormally elevated serum phosphorus levels) may contribute to progression of renal failure and is a major factor in the development of secondary hyperparathyroidism, renal osteodystrophy, and soft tissue calcification. [Block G A, Klassen P S, Lazarus J M, Ofsthun N, Lowrie E G, Chertow G. J Am Soc Nephrol 2004 August; 15(8): 2208-2218.] Prevention of phosphorus retention with dietary and pharmacological means is frequently required to prevent or reverse secondary hyperparathyroidism and the morbidities and mortality risks associated with it. [Qunibi W Y. Kidney Int 66 (Suppl 90): S8-S12. Alfrey A C. Kidney Int 66 (Suppl 90): S13-S17.] Phosphorus (Pi) binders which bind dietary phosphorus in the gastrointestinal tract are, therefore, clinical mainstays in restoring phosphorus balance and preventing hyperphosphatemia in the roughly 450,000 end-stage renal disease (ESRD) patients in the United States.

Phosphorus Binders. Phosphorus binders are ingested orally by a subject to bind dietary phosphate and convert it to insoluble phosphate salts, thus preventing its absorption from the GI tract. Phosphorus binding is a chemical reaction between dietary phosphorus and a cation of the binder compound, resulting in the formation of insoluble and hence unabsorbable phosphate compounds; adsorption of phosphorus-containing anions on the surface of binder particles; or a combination of both processes. Two classes of phosphorus binders are known: metal salts and cationic polymers. Known metal salts with phosphate-binding properties are calcium salts, including calcium acetate, calcium carbonate, calcium citrate, calcium alginate, calcium gluconate, calcium lactate, and calcium sulfate; magnesium salts, including magnesium carbonate, and magnesium hydroxide; aluminum salts, including aluminum hydroxide and aluminum carbonate; ferric citrate and ferric acetate; and lanthanum salts, including lanthanum carbonate. Cationic polymers that exhibit phosphorus binding include a polymer known as sevelamer hydrochloride (marketed as "RenaGel®" by Genzyme, Inc.).

In U.S. Pat. No. 4,889,725 Veltman discloses a means for promoting the neutralization reaction between particulate calcium carbonate and ionized phosphate by adding a material formed by the reaction of particulate calcium carbonate and dilute hydrofluoric acid. The products of this invention are useful in lowering serum phosphorus levels in patients undergoing renal dialysis, and are also useful as antacids.

A common treatment for controlling Pi levels is disclosed in U.S. Pat. No. 4,870,105 to Fordtran, which discloses a calcium acetate phosphorus binder for oral administration to an individual for the purpose of inhibiting gastrointestinal absorption of phosphorus. It further discloses a method of inhibiting gastrointestinal absorption of phosphorus, comprising administering orally the calcium acetate phosphorus binder, preferably close in time to food and beverage consumption. Likewise, U.S. Pat. No. 6,576,665 to Dennett, Jr. et al. discloses a composition for inhibiting gastrointestinal absorption of phosphorus in an individual. The composition includes a quantity of calcium acetate sufficient to bind the phosphorus and having a bulk density of between 0.50 kg/L and 0.80 kg/L and is dimensioned to form a caplet for fitting within a capsule. Further provided is a method for administering the calcium acetate composition. Likewise, U.S. Patent Application 2003/0050340 to Dennett, Jr., et al. discloses a composition for binding phosphorus within the gastrointestinal tract of an individual. The composition includes a quantity of calcium acetate having a specific bulk density sufficient to bind the phosphorus in the gastrointestinal tract of an individual. Further provided is a method for administering the calcium acetate composition.

U.S. Pat. No. 6,160,016 to DeLuca discloses a calcium formate composition for oral administration to an individual for the purpose of inhibiting gastrointestinal absorption of phosphorus. It further discloses a method of inhibiting gastrointestinal absorption of phosphorus, comprising administering orally the composition, preferably close in time to food and beverage consumption. Likewise, U.S. Pat. No. 6,489,361, to DeLuca discloses a calcium formate composition for oral administration to an individual for the purpose of inhibiting gastrointestinal absorption of phosphorus. Further, DeLuca discloses a method of inhibiting gastrointestinal absorption of phosphorus, comprising administering orally the calcium formate composition of his invention, preferably close in time to food and beverage consumption.

U.S. Pat. No. 4,689,322, to Kulbe et al. provides calcium salts or calcium mixed salts of polymeric, anionic carboxylic acids and/or an ester of sulfuric acid, and methods for their preparation and use, discloses a pharmaceutical product which contains at least a calcium salt or a calcium mixed salt of a natural or chemically modified polymeric, anionic carboxylic acid and/or an ester of sulfuric acid, and additive materials and/or carrier materials. There are further disclosed calcium salts, and methods of preparation thereof, comprised of polymannuronic acid, polygalacturonic acid, polyglucuronic acid, polyguluronic acid, the oxidation products of homoglycans, the oxidation products of heteroglycans, or their mixtures, for controlling the levels of phosphorus, calcium and iron in patients with chronic uremia and/or the control of the oxalate and/or phosphate of the blood in kidney stone prophylaxis.

U.S. Pat. No. 6,887,897 to Walsdorf and Alexandrides discloses a calcium glutarate supplement and its use for controlling phosphate retention in patients on dialysis and suffering from renal failure and associated hyperphosphatemia. Therapeutic benefit can be realized by administering a calcium glutarate compound orally to a patient to increase available calcium and contact and bind with ingested phosphorus in the patient's digestive tract, and thereby prevent its intestinal absorption.

The Pi binding properties of magnesium salts have been studied by Fine et al. in acute studies involving normal subjects. [Fine K D, Santa Ana C A, Porter J L, Fordtran J S. Intestinal absorption of magnesium from food and supplements. J Clin Invest 1991; 88: 396-402.] They found a dose-dependent decrease in Pi absorption from ingesta that ranged from 75% Pi absorption with placebo to 28% Pi absorption with 77 mEq magnesium acetate (MgAc) per os. Fine stated that Pi absorption by magnesium acetate was comparable to that of calcium acetate, a current standard of care. However, Fine rejected use of magnesium acetate, because "the risk of hypermagnesemia and diarrhea from MgAc ingestion would likely limit the clinical usefulness of MgAc as a P binder." [ibid, page 401, column 1, paragraph 4]

Several investigators have evaluated the use of orally administered magnesium (Mg) hydroxide- or carbonate-containing Pi binders in the treatment of ESRD patients undergoing dialysis. Guillot et al. treated nine patients undergoing conventional hemodialysis with oral magnesium hydroxide for three to five weeks. [Guillot A P, Hood V L, Runge C F, Gennari F J. The use of magnesium-containing phosphate binders in patients with end-stage renal disease on maintenance hemodialysis. Nephron 1982; 30:114-117.] Using doses averaging 734 mg of elemental Mg/day and concurrent dialysis with dialysate having Mg concentrations of 1.2 to 1.8 mg/dl, the serum Pi levels fell from a control (no binders) value of 9.0 mg/dL to 8.1 mg/dL as a result of treatment. The mean serum Mg levels were 4.32 mg/dL. Four of nine patients developed diarrhea. In contrast to the Guillot study, Mactier et al. observed no effect of oral choline magnesium trisalicylate (trilisate) on serum Pi levels in either hemodialysis or peritoneal dialysis patients. [Mactier R A, Leung A C T, Henderson I S, and Dobbie J W. Control of hyperphosphatemia in dialysis patients: Comparison of aluminum hydroxide, calcium carbonate, and magnesium trilisate. Dial Transplant 1987; 16: 599-601.] Adverse findings were reported by Oe et al., who studied eighteen patients undergoing conventional hemodialysis who were switched from oral $Al((OH)_3$ to $Mg(OH)_2$. [Oe P L, Lips P, van der Meulen J, de Vries P M J M, van Bronswuk H. Long-term use of magnesium hydroxide as a phosphate binder in patients on hemodialysis. Clin Nephrol 1987; 28: 180-185.] Serum Pi levels rose from 4.3 to 6.1 mg/dL despite an average daily intake of 991 mg of elemental Mg and use of a dialysate lacking Mg. The serum Mg level averaged 4.3 mg/dL during $Mg(OH)_2$ treatment. The potassium levels were significantly higher when patients received $Mg(OH)_2$ compared to the control phase (5.7±0.3 vs. 5.1±0.4 mEq/L). O'Donovan et al. switched 28 patients undergoing conventional hemodialysis from oral $Al(OH)_3$ to oral $MgCO_3$ in combination with a Mg-free dialysate. [O'Donovan R, Baldwin D, Hammer M, Moniz C, Parsons V. Substitution of aluminium salts by magnesium salts in control of dialysis hyperphosphataemia. Lancet 1986; 1: 880-882.] Over the two-year study period, Ca, P, and Mg levels were well controlled and not different from those in the control phase. The amount of elemental Mg used varied between 155 to 465 mg/day. Diarrhea was mild and transient. Similar data were reported by Moriniere et al. [Moriniere P, Vinatier I, Westeel P F. Magnesium hydroxide as a complementary aluminum-free phosphate binder to moderate doses of oral calcium in uraemic patients on chronic haemodialysis. Nephrol Dial Transplant 1988; 3: 651-656.] They also reported severe hyperkalemia as high as 8 mEq/L in many patients, the etiology of which was unclear. More recently, this same group performed a controlled study in which patients were either treated with $CaCO_3$ plus $Mg(OH)_2$ as needed or $Mg(OH)_2$ alone and 1-alpha-hydroxyvitamin $D_3$. [Morniere P, Maurouard C, Boudailliez B, Westeel P, Achard J, Boitte F, El Esper N, Compagnon M, Maurel G, Bouillon R, Pamphile R, Fournier A. Prevention of hyperparathyroidism in patients on maintenance dialysis by intravenous 1-alpha-hydroxyvitamin $D_3$ in association with $Mg(OH)_2$ as sole phosphate binder. Nephron 1992; 60: 154-163.] Neither the combination of oral calcium carbonate/magnesium hydroxide nor magnesium hydroxide alone was effective in suppressing parathyroid hormone (PTH) secretion, and uncontrolled hyperphosphatemia forced a reduction in the dose of 1-alpha-hydroxyvitamin $D_3$. Finally, Delmez et al. showed that magnesium carbonate was well-tolerated and controlled Pi and Mg levels when given in conjunction with a dialysate having a Mg concentration of 0.6 mg/dL. [Delmez J A, Kelber J, Norword K Y, Giles K S, Slatopolsky E. Magnesium carbonate as a phosphorus binder: A prospective, controlled, crossover study. Kidney Int 1996; 49: 163-167.] In addition, Delmez showed that oral magnesium carbonate (dose, 465±52 mg/day elemental Mg) allowed a decrease in the amount of elemental calcium ingested from 2.9±0.4 to 1.2±0.2 g/day (P<0.0001). Moreover, the combined treatment allowed an increase in the maximum dose of intravenous calcitriol without causing hypercalcemia.

U.S. Pat. No. 6,926,912 to Roberts et al. discloses a non-aluminum containing mixed metal compound for pharmaceutical use, which may be a mixed metal hydroxy carbonate containing magnesium and iron, and may have a hydrotalcite structure, preferably a non-aged hydrotalcite structure. Other metals, including calcium, lanthanum and cerium, may also be used. U.S. Pat. No. 4,988,569 to Okazaki et al. discloses a phosphate adsorbent comprising an magnesium oxide-titanium dioxide complex as an active ingredient and a phosphate adsorbent having said complex deposited on active carbon.

U.S. Pat. No. 5,753,706 to Hsu discloses a method of controlling phosphate metabolism and metabolic acidosis in patients suffering from renal failure and associated hyperphosphatemia or patents predisposed to development of hyperphosphatemic condition. The method comprises administering to a patient a ferric-containing compound selected from the group consisting of ferric citrate, ferric acetate, and combinations thereof. It discloses that a therapeutic benefit can be realized in accordance with such method by administering the compound orally to a patient to contact and bind with ingested phosphate in the patient's digestive tract, and thereby prevent it intestinal absorption.

U.S. Pat. No. 6,103,126, to Boos et al. provides a process for the selective elimination of inorganic phosphate from liquids by means of absorbent materials modified with polynuclear metal oxyhydroxides. Boos discloses that the absorbent materials of his invention are useful in particular for the selective elimination of inorganic phosphate from body fluids containing protein such as whole blood, plasma, liquid contents of the intestine as well as from dialysis fluid. A process for the production of pharmaceutical agents for oral application for the selective removal of inorganic phosphate is also provided, in which an absorbent material modified with polynuclear metal oxyhydroxides is coated with layer resistant to gastric acid or dispensed into an acid-resistant capsule. It further discloses that in order to selectively eliminate inorganic phosphate in an extracorporeal perfusion system, a body fluid such as whole blood or plasma is passed over one of the adsorbent materials.

In U.S. Pat. No. 5,968,976 to Murrer et al. is provided lanthanum carbonate compositions for the treatment of hyperphosphatemia. The invention further provides a method of treatment of hyperphosphatemia in a patient with renal failure, comprising the administration of an effective dose of lanthanum carbonate into the gastrointestinal tract.

Phosphate-binding polymers include sevelamer, which is marketed under the brand name RenaGel® (Genzyme, Waltham Mass.), Oxasorb®, and polymers prepared using the methods disclosed in U.S. Pat. Nos. 5,496,545, 5,667,775, 6,083,495, 6,509,013, and 6,858,203. U.S. Pat. No. 6,132,706 to Hider and Canas-Rodriguez discloses methods of medical treatment for excess phosphate using guanidine-containing polymers. U.S. Pat. Nos. 6,383,518 and 6,697,087, both to Matsuda and Kubota, disclose phosphate-binding polymer preparations. In U.S. Pat. No. 7,014,846 Holmes-Farley et al. disclose phosphate-binding polymers for oral administration.

The ideal Pi binder should bind most dietary phosphorus in the gastrointestinal tract without producing significant adverse effects. It should also be relatively inexpensive, because most dialysis patients usually consume relatively large daily doses of the binder. Unfortunately, none of the currently used Pi binders fulfill all of these requirements. It would be very useful, therefore to have a Pi binder which binds dietary phosphorus more effectively, thus enabling use of lower doses, and which does not have the risks associated with ingestion of conventional Pi binders. The present invention answers this unmet need.

SUMMARY OF THE INVENTION

In patients with impaired kidney function, the normal homeostasis of uptake and excretion of phosphates is typically impaired, leading to hyperphosphatemia and associated pathologies.

It is an object of the present invention to control the uptake of dietary phosphates to abate, ameliorate, and prevent hyperphosphatemia. It is a further object to provide a phosphate binding composition that reduces the amount of dietary phosphate absorbed from the alimentary tract to achieve and sustain a balance of phosphate systemically in the body of a mammal. It is a still further object to provide phosphate binders that obviate side effects of conventional binders such as magnesium acetate and calcium acetate, which may cause diarrhea or constipation, respectively, or gastric irritation.

The present invention provides a composition for reducing the amount of dietary phosphorus absorbed from the alimentary tract comprising a cationic phosphate binder and a dithiolane carboxylate salt. The cationic phosphate binder may be calcium acetate, calcium carbonate, calcium citrate, calcium alginate, calcium gluconate, calcium lactate, calcium sulfate, calcium succinate, a lanthanum salt, a cationic polymer, and combinations thereof. Of particular efficacy in scavenging dietary phosphate are combinations of hydrophilic and lipophilic compounds. Therefore, in a preferred embodiment, a relatively hydrophilic phosphate binder such as calcium acetate, calcium gluconate, calcium lactate, or calcium succinate is combined with a dithiolane carboxylate salt in a capsule, pill, or elixir, or as a direct additive to food. The dithiolane carboxylate salt in such embodiment will have an aliphatic content of a 4-8 carbon chain, and has the following structure:

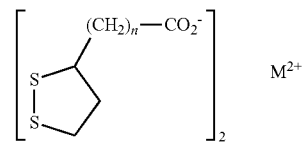

wherein M is a cation of valence 2 and n is an integer 4-8. Said cations M include $Mg^{++}$, $Ca^{++}$, and lanthanum. In certain preferred embodiments of the present invention, the aliphatic content of the carbon chain of the dithiolane carboxylate molecule may vary from 4 carbon atoms to about 8 carbon atoms. The aliphatic content of the dithiolane carboxylate molecule, however, may vary from one carbon atom to about 8 carbon atoms. A most preferred embodiment of the dithiolane carboxylate salt is magnesium lipoate (wherein n is 4), which in addition to its phosphorus binding has therapeutically beneficial antioxidant properties.

In certain embodiments, a phosphate binding composition of the present invention comprises a calcium salt and a dithiolane carboxylate salt wherein the dithiolane carboxylate salt is a magnesium dithiolane carboxylate salt. Preferably, in these embodiments the calcium salt and the magnesium dithiolane carboxylate salt are administered orally in a ratio of about 6:1 to 1:6 by molar weight.

In the method of the present invention, a composition as described hereinabove is administered to a mammal by oral ingestion either concomitantly with food or close in time to the consumption of dietary phosphate-containing food or beverage. The composition, so administered, may be regarded either as a food additive or a drug within the meaning of title 21 of the Code of Federal Regulations (CFR).

DETAILED DESCRIPTION OF THE INVENTION

The present invention relates to a composition comprising a dithiolane carboxylate salt and a cationic phosphate binder for oral administration to a subject. The composition is useful for reducing phosphorus absorption from the GI tract.

The present invention also relates to a method of inhibiting gastrointestinal phosphorus absorption. The method of the present invention is based on the demonstration that a composition comprising a first quantity of a dithiolane carboxylate salt and a second quantity of a cationic phosphate-binding agent is an effective binder of dietary phosphorus when the composition is administered orally to a subject. The method comprises orally administering a quantity of the composition sufficient to bind with phosphorus in the GI tract and prevent its absorption. Preferably, the dose of the composition is between about 0.1 and 15 g and is administered in a pharmaceutically acceptable oral dosage form (i.e., a tablet, gelatin capsule, elixir, and so forth). In a most preferable embodiment of the present invention, the oral dose is ingested close in time with food and/or beverage consumption.

In addition, the present invention relates to a method of reducing serum phosphorus levels in a warm-blooded animal comprising treating the animal with a therapeutically effective amount of a composition comprising a first quantity of a dithiolane carboxylate salt and a second quantity of a cationic phosphate binder.

The term "phosphorus," in defining use of the composition as a phosphorus binder, is intended to embrace both inorganic and organic anions of phosphorus in the various forms that are capable of electrostatic reaction with a phosphorus-binding agent including, by way of example, phosphate ($H_2PO_4^{1-}$, $HPO_4^{2-}$, and $PO_4^{3-}$), pyrophosphate ($P_2O_7^{4-}$), and the like.

The term "phosphate," in defining use of the composition as a phosphate binder, is intended to embrace both inorganic and organic anions of phosphorus in the various forms that are capable of electrostatic reaction with a phosphate-binding agent including, by way of example, phosphate ($H_2PO_4^{1-}$, $HPO_4^{2-}$, and $PO_4^{3-}$), pyrophosphate ($P_2O_7^{4-}$), and the like.

The term "phosphorus binding agent" or "phosphorus binder" or "phosphate binder," as it relates to the present invention, includes, by way of example, calcium salts such as calcium carbonate, calcium acetate, calcium citrate, calcium formate, calcium gluconate, calcium lactate, calcium glutarate, or calcium succinate. These terms also include, by way of example, magnesium salts such as magnesium carbonate, magnesium hydroxide, magnesium acetate, and magnesium succinate; as well as lanthanum salts, such as lanthanum carbonate. Also within the scope of this invention are hydrates, crystalline forms, and polymorphic forms of the aforementioned metal salts, metal salt-containing compositions having specific bulk densities or tap densities, and metal-salt containing compositions having specific particle sizes. Further included within the scope of this invention are metal salt-containing compositions coated with pharmaceutically acceptable materials intended to modify the release and/or bioavailability of the metal salt (e.g., Eudragit, microcrystalline cellulose, hydroxypropylmethylcellulose phthalate, and so forth).

The term "phosphorus binding agent" or "phosphorus binder" or "phosphate binder," as it relates to the present invention, also includes cationic polymers that bind phosphate, including by way of example, sevelamer, sevelamer hydrochloride, a polymer marketed as RenaGel®, a cationic polymer that is marketed under the brand name Oxasorb®, and polymers prepared using the methods disclosed in U.S. Pat. Nos. 5,496,545, 5,667,775, 6,083,495, 6,132,706, 6,383,518, 6,509,013, 6,697,087, 6,858,203 and 7,014,846.

By the term "dithiolane carboxylate salt" is meant a compound having the general formula:

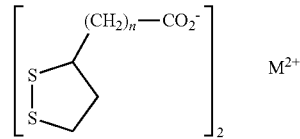

wherein M is a cation of valence 2 and n is an integer from 1 to 8. In general, dithiolane carboxylic acids may be purchased from chemical supply houses or may be prepared as described by Guillonneau et al. [Guillonneau, C, Charton, Y, Ginot, Y-M, Fouquier-d'Herouel, M-V, Bertrand, M, Lockhart, B, Lestage, P, and Goldstein, S. 2003. Synthesis and pharmacological evaluation of new 1,2-dithiolane based antioxidants. Eur J Med Chem 38: 1-11.] A dithiolane carboxylic acid is converted to a metal dithiolane carboxylate salt by reacting a metal oxide, metal bicarbonate, metal carbonate, or metal hydroxide with a dithiolane carboxylic acid in a lower alcohol solution, as disclosed by Trusovs in U.S. Pat. No. 6,670,494. A preferred dithiolane carboxylate salt is magnesium lipoate, the magnesium salt of lipoic acid, wherein n is 4. Lipoic acid (Chemical Abstracts Service Registry No. 62-46-4; principal names: alpha-lipoic acid, thioctic acid and 1,2-dithiolane-3-pentanoic acid) is the starting material for the preparation of magnesium lipoate as disclosed above. Lipoic acid is a chiral compound that was first isolated and identified in 1950. The compound is commercially available as racemic α-lipoic acid, enantiopure R-(+)- or S-(−)-α-lipoic acid, mixtures thereof, as well as the reduced counterpart racemic dihydrolipoic acid (6,8-dimercaptooctanoic acid), enantiopure R-(−)- or S-(+)-dihydrolipoic acid, and mixtures thereof. In accordance with the present invention, the term "magnesium lipoate" includes the magnesium salt of racemic α-lipoic acid, enantiopure R-(+)- or S-(−)-α-lipoic acid, mixtures thereof, as well as the reduced counterpart racemic dihydrolipoic acid (6,8-dimercaptooctanoic acid), enantiopure R-(−)- or S-(+)-dihydrolipoic acid, and mixtures thereof.

According to the method of the present invention, the composition of the present invention is administered, alone or in combination with other substances (e.g., along with materials necessary to form a tablet or caplet as a delivery vehicle for the composition or in a hard gelatin capsule) in sufficient quantities to reduce phosphorus absorption from the gastrointestinal tract. The composition is administered orally, preferably close in time to food and/or beverage consumption (i.e., concurrent with and/or within about 1 hour before or after ingestion of food or beverages). The composition is ingested after sprinkling or distributing on or in food or beverages, either before or after food preparation, or is ingested as a pharmaceutical dosage form, preferably a tablet, caplet or capsule.

The term "excipient material" is intended to mean any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms or conditions.

The phrase "therapeutically effective" is intended to qualify the amount of the composition of the present invention for use in the orally administered therapy which will achieve the goal of reducing elevated serum phosphorus levels by controlling, abating, ameliorating, reducing or preventing, for example, the absorption of phosphorus from ingesta in the gastrointestinal tract, while avoiding adverse side effects typically associated with metal-containing phosphorus binding agents.

Included within the scope of this invention is a method of treating hyperphosphatemia in a warm-blooded animal using pharmaceutical compositions comprising a dithiolane carboxylate salt, a cationic phosphate binder, and a suitable pharmaceutical carrier.

For the purpose of this disclosure, a warm-blooded animal is a member of the animal kingdom which includes but is not limited to mammals and birds. The most preferred mammal of this invention is human.

Phosphorus binding is a chemical reaction between a cationic phosphate binder and dietary phosphorus, which encompasses both inorganic and organic anions of phosphorus in the various forms that are capable of electrostatic reaction with a cationic phosphate-binding agent including, by way of example, phosphate ($H_2PO_4^-$, $HPO_4^{2-}$, and $PO_4^{3-}$), pyrophosphate ($P_2O_7^{4-}$), resulting in the formation of insoluble and hence unabsorbable phosphate compounds; adsorption of phosphorus-containing anions on the surface of binder particles; or a combination of both processes. In general, conventional phosphate binders comprise a single cationic substance, i.e., a calcium salt, a magnesium salt, a lanthanum salt, an aluminum salt, or a cationic polymer effective for phosphate binding such as RenaGel®. Surprisingly, the inventor has discovered that a composition comprising two phosphate binders provides unexpected and synergistic phosphorus binding action as well as significant and distinct pluripotent therapeutic benefits to a subject requiring treatment for hyperphosphatemia, as compared to conventional Pi binders.

One embodiment of the present invention, for example, is a composition comprising a calcium salt and a magnesium dithiolane carboxylate salt. In this embodiment, both the calcium ion and the magnesium ion bind phosphorus in ingesta and prevent its absorption from the gastrointestinal tract. Preferred embodiments of the present invention include compositions in which the calcium salt is calcium acetate, calcium carbonate, calcium citrate, calcium alginate, calcium gluconate, calcium lactate, calcium sulfate, calcium succinate, or combinations thereof, and the magnesium salt is magnesium lipoate. More preferred embodiments of the present invention comprise a first quantity of a hydrophilic calcium salt (Table 1) selected from the group consisting of calcium acetate, calcium gluconate, calcium lactate, calcium succinate, or combinations thereof, and a second quantity of the dithiolane carboxylate salt, a lipophile that binds phosphate and has therapeutically beneficial antioxidant properties. Such a more preferred composition provides a cationic phosphate binder that is a hydrophile (in other words, a cationic phosphate binder that has a solubility in water that exceeds about 0.5 g/100 mL of water) and binds phosphate in hydrophilic environments and a second, lipophilic phosphate binder, the metal dithiolane carboxylate, which binds phosphate in lipophilic environments.

TABLE 1

Examples of Cationic Phosphate Binders that are Relative Hydrophiles*

| Metal Salt | Solubility in Water | Hydrophile? |
|---|---|---|
| Calcium Acetate | 37.4 g/100 mL | Yes |
| Calcium Carbonate | 0.0013 g/100 mL | No |
| Calcium Citrate | 0.10 g/100 mL | No |
| Calcium Gluconate | 3.72 g/100 mL | Yes |
| Calcium Lactate | 5.4 g/100 mL | Yes |
| Calcium Succinate | 1.28 g/100 mL | Yes |
| Calcium Sulfate | 0.20 g/100 mL | No |
| Lanthanum Sulfate | 2.92 g/100 mL | Yes |
| Magnesium Acetate | 53.4 g/100 mL | Yes |
| Magnesium Carbonate | 0.01 g/100 mL | No |
| Magnesium Hydroxide | 0.00125 g/100 mL | No |
| Magnesium Lactate | 4 g/100 mL | Yes |
| Magnesium Oxide | No measurable solubility | No |
| Magnesium Sulfate | 27.2 g/100 mL | Yes |

*Data are taken from Lange's Handbook of Chemistry, 15th edition, Dean JA, ed. McGraw Hill, Inc., New York, 1999.

Most preferred embodiments of the present invention include compositions in which the calcium salt is calcium succinate or calcium acetate and the magnesium salt is magnesium (R)-(+)-lipoate. The advantages of such embodiment of the present invention as compared to conventional phosphate binders include the following: (a) Both calcium and magnesium ions bind phosphorus in ingesta and prevent its absorption from the gastrointestinal tract. (b) The quantity of calcium salt in this embodiment is independent of the quantity of the magnesium salt of the present invention. Advantageously, therefore, the quantity of calcium salt that is employed may be selected to maximize phosphorus binding and minimize transfer of calcium ion to the systemic circulation, uptake that is believed to cause vascular calcification. Further, the quantity of magnesium lipoate that is employed may be selected to maximize phosphorus binding and minimize transfer of magnesium ion to the systemic circulation, uptake that is believed to cause hypermagnesia. (c) The quantity of calcium salt and the quantity of magnesium lipoate in this embodiment may be selected to maximize phosphorus binding and minimize the side effects of constipation caused by calcium ion and the side effects of diarrhea caused by magnesium ion. (d) The quantity of calcium salt and the quantity of magnesium lipoate in this embodiment may be selected to maximize phosphorus binding and minimize the side effects of kidney dysfunction and bone disorders caused by an excess of calcium ion relative to magnesium ion in the serum. (e) If the composition of this embodiment of the present invention comprises a first quantity of calcium succinate and a second quantity of magnesium lipoate, advantageously the composition does not cause acid reflux, vinegar breath, or undesirable gastric irritation in the subject, as does the conventional phosphate binder calcium acetate. In addition, if the composition of this embodiment of the present invention comprises a first quantity of calcium succinate and a second quantity of magnesium lipoate, an additional mechanism of phosphate binding applies, leading to the formation of octacalcium phosphate succinate salts that remain in the gastrointestinal tract. This mechanism does not apply if the calcium salt is calcium acetate, calcium citrate, or calcium carbonate. [Marković M, Fowler B O, Brown W E. Octacalcium phosphate carboxylates. 1. Preparation and identification. Chem Mater 1993; 5: 1401-1405. Marković M, Fowler B O, Brown W E. Octacalcium phosphate carboxylates. IV. Kinetics of formation and solubility of octacalcium phosphate succinate. J Cryst Growth 1994; 135: 533-538. Marković M, Fowler B O, Brown W E. Octacalcium phosphate carboxylates. 2. Characterization and structural considerations. Chem Mater 1993; 5: 1406-1416.] Preferred quantities of calcium salt and magnesium lipoate in this embodiment of the present invention comprise molar ratios of calcium salt to magnesium lipoate in the range from about 0.1 moles of calcium salt to about 6 moles of magnesium lipoate to about 6 moles of calcium salt to about 0.1 moles of magnesium lipoate. Particularly preferred quantities of calcium salt and magnesium lipoate in this embodiment of the present invention comprise molar ratios of calcium salt to magnesium salt in the range from about 2 to about 5 moles of calcium salt for each mole of magnesium lipoate.

Another embodiment of the present invention, for example, is a composition comprising a lanthanum salt and a dithiolane carboxylate salt. In this embodiment, both the lanthanum ion and the metal ion of the dithiolane carboxylate salt bind phosphorus in ingesta. Preferred embodiments of the present invention include compositions in which the lanthanum salt is lanthanum acetate, lanthanum carbonate, lanthanum sulfate, or lanthanum succinate and the dithiolane carboxylate salt is magnesium lipoate. Particularly preferred embodiments of the present invention include compositions in which the lanthanum salt is lanthanum carbonate and the dithiolane carboxylate salt is magnesium (R)-(+)-lipoate. The advantages of this embodiment of the present invention as compared to conventional phosphate binders include the following: (a) Both lanthanum and magnesium ions bind phosphorus in ingesta and prevent its uptake from the gastrointestinal tract. (b) The quantity of lanthanum salt in this embodiment is independent of the quantity of magnesium salt. Therefore, in this embodiment of the present invention, the quantity of lanthanum salt may be selected to maximize phosphorus binding and minimize transfer of lanthanum ion to the systemic circulation, uptake which has the potential to cause harm to the subject. The quantity of magnesium salt may be selected to maximize phosphorus binding and minimize transfer of magnesium ion to the systemic circulation, uptake which is believed to cause hypermagnesia. (c) The quantity of the magnesium salt of the present invention may be selected to allow a reduced quantity of a lanthanum salt to be employed for phosphorus binding, as compared to the quantity required in conventional phosphate binding compositions containing a lanthanum salt.

Yet another embodiment of the present invention, for example, is a composition comprising a cationic phosphate-binding polymer and a dithiolane carboxylate salt. By way of example, cationic phosphate-binding polymers that are useful in this embodiment of the present invention include sevelamer, which is marketed under the brand name RenaGel® (Genzyme, Waltham Mass.), a cationic polymer that is marketed under the brand name Oxasorb®, and polymers prepared using the methods disclosed in U.S. Pat. Nos. 5,496,545, 5,667,775, 6,083,495, 6,132,706, 6,383,518, 6,509,013, 6,697,087, 6,858,203 and 7,014,846. In this embodiment, both the cationic polymer and the metal ion of the dithiolane carboxylate salt bind phosphorus in ingesta. The quantity of the dithiolane carboxylate salt of the present invention may be selected to allow ingestion of a reduced quantity of the cationic polymer, as compared to the quantity required in conventional dosage forms of the cationic polymer, thereby advantageously reducing undesirable side effects caused by the polymer. Preferred embodiments of the present invention include compositions in which the cationic polymer is sevelamer hydrochloride, sevelamer acetate, sevelamer maleate, sevelamer bicarbonate, or sevelamer, and the dithiolane carboxylate salt is magnesium lipoate. Particularly preferred embodiments of the present invention include compositions in which the cationic polymer is sevelamer hydrochloride and the magnesium salt is magnesium (R)-(+)-lipoate. The advantages of this embodiment of the present invention as compared to conventional phosphate binders include the following: (a) Both the cationic polymer and metal ion of the dithiolane carboxylate salt bind phosphorus in ingesta. (b) The quantity of cationic polymer in this embodiment is independent of the quantity of metal dithiolane carboxylate salt. Advantageously, therefore, the quantity of cationic polymer that is employed may be selected to maximize phosphorus binding and minimize undesirable side effects caused by the cationic polymer, such as gastric irritation or nausea. Further, the quantity of magnesium lipoate that is employed in some embodiments may be selected to maximize phosphorus binding and minimize transfer of magnesium ion to the systemic circulation, uptake that is believed to cause hypermagnesia.

A composition of the present invention comprises a first quantity of a cationic phosphate binder and a second quantity of a dithiolane carboxylate salt, wherein the combination of the first quantity and the second quantity comprises a therapeutically effective quantity of a phosphate-binding composition of the present invention. A preferred composition of the present invention is a composition comprising a first quantity of a cationic phosphate binder and a second quantity of magnesium lipoate, wherein the combination of the first quantity and the second quantity comprises a therapeutically effective quantity of a phosphate-binding composition of the present invention. A particularly preferred composition of the present invention is a composition comprising a first quantity of a cationic phosphate binder and a second quantity of magnesium (R)-(+)-lipoate, wherein the combination of the first quantity and the second quantity comprises a therapeutically effective quantity of a phosphate-binding composition of the present invention.

As compared to conventional magnesium salts that are used as phosphate binders, a magnesium dithiolane carboxylate salt provides significant and distinct advantages that include the following. A magnesium dithiolane carboxylate salt has physicochemical properties related to its structure that render it both hydrophilic and lipophilic, as compared to a conventional magnesium salt which is hydrophilic (Table 1). Therefore, a magnesium dithiolane carboxylate salt of the present invention will bind phosphate that is present in both hydrophilic and lipophilic environments. Magnesium lipoate is the magnesium dithiolane carboxylate salt component in phosphorus binding compositions that are preferred embodiments of the present invention. Surprisingly, the inventor has discovered that magnesium lipoate is a phosphorus binder. In addition, the inventor has found that magnesium lipoate is a source of lipoate, the anion of lipoic acid. Hypertension, diabetes, and heart disease are serious co-morbidities to renal disease and accelerate physiological dysfunction, a decline in the quality of life, and death. Administration of lipoic acid to a subject having hypertension, diabetes, heart disease or renal disease is known to reduce the cellular and tissue dysfunction that characterizes each of these disease states. [(a) Fuchs, J, Packer, L and Zimmer, G. (Eds), 1997. *Lipoic Acid in Health and Disease*, Marcel Dekker, New York. (b) Borcea, V, Nourooz-Zadeh, J, Wolff, SP, Klevesath, M, Hofmann, M, Urich, H, Wahl, P, Ziegler, R, Tritschler, H, Halliwell, B. et al. 1999. a-Lipoic acid decreases oxidative stress even in diabetic patients with poor glycemic control and albuminuria. Free Radic Biol Med 26: 1495-1500. (c) Wollin, S D, and Jones, P J. 2003. Alpha-lipoic acid and cardiovascular disease. J Nutr 133(11): 3327-3330. (d) Kagan, V E, Shvedova, A, Serbinova, E, Khan, S, Swanson, C, Powell, R, and Packer, L. 1992. Dihydrolipoic acid—a universal antioxidant both in the membrane and in the aqueous phase. Reduction of peroxyl, ascorbyl and chromanoxyl radicals. Biochem Pharmacol 44: 1637-1649.] However, lipoic acid is unstable during storage, and (R)-(+)-lipoic acid is even more unstable during storage.

In contrast to the instability of lipoic acid, the inventor has discovered that either magnesium lipoate or magnesium (R)-(+)-lipoate is stable during storage. (R)-(+)-Lipoic acid is the form of lipoic acid in the body. Therefore, magnesium (R)-(+)-lipoate is the most preferred form of magnesium lipoate in a composition of the present invention.

DOSAGE FORMS. The compositions of this invention can be administered by any means that effects contact of the therapeutically active ingredients (i.e., active ingredients) with the site of action in the body of a warm-blooded animal. A most preferred administration is by the oral route (i.e., ingestion). The active ingredients can be administered by the oral route as particles that are sprinkled or distributed on or in food or are dissolved or suspended in beverages or can be provided in pharmaceutical solid dosage forms, such as tablets, capsules, and powders, or in liquid dosage forms, such as elixirs, syrups, and suspensions. The pharmaceutical composition is preferably made in the form of a dosage unit containing a particular amount of each active ingredient.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy.* 20$^{th}$ Edition. Baltimore: Lippincott, Williams & Williams, 2000]. For therapeutic purposes, the active components of this invention are ordinarily combined with one or more excipients appropriate to the indicated route of administration. Such capsules or tablets may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Serum phosphorus levels rise easily after a large meal. Therefore, dosing for oral administration preferably comprises a regimen calling for administration of a therapeutic dose of calcium succinate close in time to the ingestion of food and/or beverages. Dosing may be subdivided in a manner in which a portion of the prescribed dose is ingested prior to consumption of food or beverages, another portion is ingested together with food or beverages, and yet other portions are ingested close in time after ingestion of food or beverages. Preferably, dosing occurs within about an hour prior to and after ingestion of food or beverages.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLE 1

Theoretical calculations of Phosphorus (Pi) binding as a measure of its ability to form phosphate salts. Phosphorus binding results from reaction of a cation with Pi to form an insoluble cation-phosphate salt. Equilibrium constant expressions for the chemical reactions involved in the interactions of Pi and calcium salts (Table 2) have been used to calculate theoretical binding of Pi by calcium succinate. Theoretical calculations are based on the chemical reaction in which inorganic phosphate ($H_2PO_4^{1-}$, $HPO_4^{2-}$, and/or $PO_4^{3-}$) that is in solution with a metal ion reacts to form insoluble metal phosphate salts.

In the discussion that follows, binding at equilibrium has been estimated by calculating the total amount of phosphate that could exist in a saturated solution of the binder cation-phosphate precipitate in the presence of the excess binder at the particular pH of interest. The binding reaction is the formation of the insoluble phosphate(s): $aB+bP=B_aP_b$ (S) (where B=binder cation, $P=PO_4^{3-}$ or $HPO_4^{2-}$, s=solid or precipitate form, a=mol of B, b=mol of P). The concentration at equilibrium was assumed to be governed by the solubility product constant, $K_{sp}=[B]^a[P]^b$, were [X] denotes molar concentration of component X in a saturated solution, and $K_{sp}$ is the solubility product constant for the reaction (Table 2). Total phosphate concentration was obtained by simultaneous solution of the solubility product constant expressions and the equilibrium constant expressions governing the relative amounts of inorganic phosphate species ($H_3PO_4$, $H_2PO_4^-$, $HPO_4^{2-}$, $PO_4^{3-}$). The possibility that the binder cation formed soluble complexes with other species in solution, such as succinate, was also considered in the system of equations solved for determining total phosphate. For these calculations, the effect of ionic strength was ignored, and activity coefficients were assumed to be unity. Percent binding was calculated as precipitated phosphate divided by total phosphate times 100.

TABLE 2

Equilibria and related equilibrium constants

| Equilibrium | Log $K_{SP}$ | Eq. No. |
|---|---|---|
| $HPO_4^{2-} + H^+ = H_2PO_4^{1-}$ | 6.83 | (1) |
| $PO_4^{3-} + H^+ = HPO_4^{2-}$ | 11.72 | (2) |
| $H(Succ)^{1-} + H^+ = H_2(Succ)$ | 3.92 | (3) |
| $(Succ)^{2-} + H^+ = H(Succ)^{1-}$ | 5.29 | (4) |
| $Ca^{2+} + H_2PO_4^{1-} = CaH_2PO_4^{1+}$ | 1.06 | (5) |
| $Ca^{2+} + HPO_4^{2-} = CaHPO_4$ | 1.90 | (6) |
| $Ca^{2+} + H(Succ)^{1-} = CaH(Succ)^{1+}$ | 0.54 | (7) |
| $Ca^{2+} + (Succ)^{2-} = Ca(Succ)$ | 1.25 | (8) |

The binding of phosphorus by calcium succinate at pH 5 will be taken as an example. If the initial total phosphate concentration is 0.0172 M (or 320 mg/600 mL) and that of $Ca^{2+}$ is 0.0625 M (or 1,500 mg/600 mL, the equilibrium constant expressions (Table 2) governing the hydrogen-phosphate equilibria may be used to calculate the concentration of various forms of phosphate at pH 5. At pH 5, the dominant form of succinate is $H(Succ)^{-1}$. Therefore, the calcium-succinate equilibrium is defined by the following reactions and their solubility product constant expressions ($K_{sp}$):

$$Ca^{2+}+(Succ)^{-2}=Ca(Succ)(s) \quad K_{sp}=9.77 \tag{9}$$

$$Succ^{2-}+H^+=H(Succ)^{-1} \quad K_{sp}=1.45 \times 10^5 \tag{10}$$

Combining Equations 9 and 10:

$$Ca(Succ)(s)+H^+=Ca^{2+}+H(Succ)^{-1} \quad K_{sp}=1.48 \times 10^4 \tag{11}$$

Note that $K_{sp}$ is large, indicating that the equilibrium in Eq. 11 rests largely to the right. On this basis, it is chemically reasonable to assume that the calcium ion is fully available to bind with phosphate.

At pH 5, the dominant form of phosphate is $H_2PO_4^{1-}$. Using the concentrations above for the precipitation of $CaHPO_4$ and $Ca_3(PO_4)_2$, it may be shown that only $CaHPO_4$ would precipitate. The following reactions occur at equilibrium:

$$CaHPO_4(s)=Ca^{2+}+HPO_4^{2-} \quad K_{sp}=4 \times 10^{-7} \tag{12}$$

$$HPO_4^{2-}+H^+=H_2PO_4^{1-} \quad K_{sp}=1.47 \times 10^7 \tag{13}$$

Combining Equations 12 and 13, we obtain:

$$CaHPO_4(s)+H^+=Ca^{2+}+H_2PO_4^{1-} \tag{14}$$

for which $$K_{SP} = \frac{[Ca^{2+}][H_2PO_4^{1-}]}{[H^+]} = 5.9 \tag{15}$$

If $K_{sp}$ for $CaHPO_4$ were zero, all of the phosphate (0.0172 M) would precipitate as $CaHPO_4$, and there would be (0.0625−0.0172) M of calcium in solution. Because $K_{sp}$ is not zero, an additional amount, x mol of calcium and phosphate, remains in solution. Hence, at equilibrium, $[H_2PO_4^{1-}]$=x and $[Ca^{2+}]$=(0.0625−0.0172)+x. Substituting these values in Equation 16 and solving: x=0.00127 M at pH 5. The concentration of phosphate in the precipitate=(0.0172−x)=(0.0172−0.00127)=0.0159 M, and the percent binding=(phosphate in precipitate/total phosphate)×100=(0.0159/0.0172)×100=92.4%. These calculations indicate that calcium succinate is an excellent phosphate binder.

Similar calculations have been performed for calcium carbonate and calcium acetate. [Sheikh M S, Maguire J A, Emmett M, Santa Ana C A, Nicar M J, Schiller L R, Fordtran J S. Reduction of dietary phosphorus absorption by phosphorus binders: A theoretical, in vitro, and in vivo study. J Clin Invest 1989; 83: 66-73.45.] Similar results are expected when calculations are performed in like manner for magnesium lipoate, an embodiment of a magnesium dithiolane carboxylate of the present invention.

EXAMPLE 2

In vitro Assessment of Phosphate (Pi) Binding by Calcium Succinate. Test Preparations: Solutions of the test article (calcium succinate) and control articles (calcium acetate) were prepared in deionized, purified water having 18 MΩ or greater resistance. The pH of each solution was adjusted to the desired value by the addition of concentrated hydrochloric acid or sodium hydroxide, as appropriate.

Tests and Assays: Calcium succinate was assayed as described in the U.S. Pharmacopoeia by dissolving an accurately weighed sample in water containing hydrochloric acid, adding hydroxynapthol blue as an indicator, and titrating to a blue endpoint with edetate disodium solution. An HPLC method with conductivity detection was developed and validated for use in the determination of succinate, acetate and phosphate. The separation was performed on a Dionex AS11 Cation-Exchange HPLC column integrated with an Agilent Series 1100 HPLC system, and detection of the anionic species was enabled using a Dionex ED50 Electrochemical Detector, operating in Conductivity Mode. Limits of Detection and Quantitation were enhanced through the use of a Dionex Anion Self-Regenerating Suppressor. After assay-specific development and verification of assay performance were completed, the analysis of phosphate and succinate or acetate was performed by sampling the test solution and diluting it, if necessary, to a concentration within the linear range of the Assay. The sample was then injected onto the HPLC column and eluted with a sodium hydroxide gradient. Data were acquired using Agilent ChemStation® software.

Experimental Methods: 1.43 g of $NaH_2PO_4.H_2O$ (equivalent to 329 mg of elemental phosphorus present as phosphate) was dissolved in 570 mL of deionized water. The test or control binder was dissolved in deionized water to a volume of 30 mL. The binder solution was added to the phosphorus solution to give a final volume of 600 mL. For each binder study, the phosphorus solutions were titrated by addition of concentrated HCl or NaOH to two different initial pH levels: 4 and 6. Published reports indicate that a drift in pH over time may be observed, and the solutions were re-titrated to their initial pH immediately after addition of the binder solution and again 1 and 24 h thereafter. During titrations the mixture was stirred with a magnetic stirrer at ~100 rpm for ~1 min. Then the beakers containing the solutions were covered with plastic wrap and placed in a shaker bath at 37° C., shaking at ~20 cycles per minute. This stirring rate was selected because in vitro antacid activity at such low stirring rates has been reported to correlate well with in vivo antacid activity in the stomach. Samples for the HPLC assay of succinate and Pi (or acetate and Pi) were taken just before titrations to the initial pH and at 1, 4, and 10 h post-mixing; these later intervals have been reported to correspond to the approximate residence time in stomach, the time available for absorption in the small intestine, and the maximum time available for phosphorus binding that have been reported in related in vivo studies, respectively. Then the samples were centrifuged at 3,000 rpm for 30 min. The supernatant was filtered sequentially though filter paper (#50; Whatman, Inc., Clifton, N.J.) and then through a 0.2 μm pore-size filter (e.g., Millipore Corp., Medford, Mass.) before analysis. (No interference by the filtration processes was observed in preliminary experiments.) The decrease in phosphorus concentration from the original concentration in the phosphorus solution to that of the filtrate represents the bound phosphorus. This was expressed as percent of the total phosphorus present in the original solution. The experiments were stopped when either 100% phosphorus binding was achieved, or no more than 5% increase in binding was observed over a 6-7 day period of further incubation.

The experimental data showed that the extent of phosphate binding at each value of solution pH by calcium succinate was equal to or greater than that of calcium acetate (Table 3).

TABLE 3

Observed in vitro Pi binding for calcium compounds at pH 6

| Calcium Source | % Ca, by weight | Observed in vitro Pi Binding, % | | Comments |
| --- | --- | --- | --- | --- |
| | | pH 4.0 | pH 6.0 | |
| Calcium Acetate | 23% | 58.6% | 93.8% | Inventor's findings (Note 1); confirm data of Sheikh et al. (NOTE 2) |
| Calcium Succinate | 25% | 59.4% | 94.0% | Inventor's discovery (Note 1) |
| Calcium Carbonate | 40% | Not Reptd. | 90 | NOTE 2 |
| Calcium Citrate | 21% | Not Reptd. | 10 | 20% at pH 6.5 (NOTE 2) |
| Calcium Formate | 31% | Not Reptd. | Not Reptd. | Not reported. |
| Calcium Lactate | 14% | Not Reptd. | 90 | NOTE 2 |
| Calcium Gluconate | 9.3% | Not Reptd. | 90 | NOTE 2 |

(Note 1) Mean values of triplicate determinations of phosphate and acetate or succinate by anion-exchange HPLC with conductivity detection.
(NOTE 2) Sheikh MS, Maguire JA, Emmett M, Santa Ana CA, Nicar MJ, Schiller LR, Fordtran JS. Reduction of dietary phosphorus absorption by phosphorus binders: A theoretical, in vitro, and in vivo study. J Clin Invest 1989; 83:66-73.

The data in Table 3 confirm that Pi binding by both calcium acetate and calcium succinate occurs at values of pH as low as pH 4.0 but is nearly quantitative at values of pH near neutrality. Note as well that these in vitro data fail to predict the differences in Pi binding by the various calcium salts that are observed in vivo, nor do these in vitro data reveal the poor dissolution of calcium carbonate in the stomach and the "vinegar breath" associated with ingestion of calcium acetate. Neither of these shortcomings is observed when calcium succinate of the present invention is used as a Pi binder.

Similar in vitro studies have been completed to show that calcium and aluminum salts are effective phosphate binders. [Sheikh M S, Maguire J A, Emmett M, Santa Ana C A, Nicar M J, Schiller L R, Fordtran J S. Reduction of dietary phosphorus absorption by phosphorus binders: A theoretical, in vitro, and in vivo study. J Clin Invest 1989; 83:66-73.] Likewise, similar in vitro studies have been completed to show that cationic polymers are effective phosphate binders. [Bleyer A J, Burke S K, Dillon M, et al. A comparison of the calcium-free phosphate binder sevelamer hydrochloride with calcium acetate in the treatment of hyperphosphatemia in hemodialysis patients. Am J Kidney Dis 1999; 33: 694-701.]

EXAMPLE 3

Phosphate Binding by Magnesium Salts. This study was reported by Fine et al. [Fine K D, Santa Ana C A, Porter J L, Fordtran J S. Intestinal absorption of magnesium from food and supplements. J Clin Invest 1991; 88: 396-402.] Magnesium absorption over a wide range of intakes to which the intestine may be exposed from magnesium-containing medications was measured in eight healthy male subjects, aged 25-35 years old, after they ingested a standard meal supplemented with 0, 10, 20, 40, and 80 mEq of magnesium acetate. (Data in Table 4 are taken from Table 3, page 399 of the Fine et al. publication.) These data show that although absorption increased with each increment in intake, fractional magnesium absorption fell progressively from 65% at the lowest to 11% at the highest intake. These results are compatible with a mechanism of magnesium absorption that reaches an absorptive maximum, together with a mechanism that endlessly absorbs a defined fraction (7%) of ingested magnesium. Compared to calcium absorption, much less magnesium than calcium was absorbed at magnesium acetate intakes above 8 mEq/meal, apparently due to greater restriction of intestinal permeability to magnesium. Further, increasing amounts of magnesium acetate ingested with the standard meal caused progressive and significant decreases in net and fractional phosphorus absorption ($r=-0.73$, $P \leq 0.001$). Net calcium absorption from the standard meal was unaffected by increasing amounts of magnesium acetate. However, urinary calcium excretion increased as magnesium acetate supplementation increased, and at the highest supplemental dose of magnesium acetate, 10-h calcium excretion exceeded net calcium absorption. Compared to 50 mEq of calcium acetate, which reduced the fractional absorption of dietary Pi from 77% to 26%, 50 mEq of magnesium acetate would reduce fractional Pi absorption from 77% to 34%. In concluding remarks (column 1 page 401), the authors stated, "Unfortunately, the risk of hypermagnesemia and diarrhea from magnesium acetate ingestion would likely limit the clinical usefulness of magnesium acetate as a Pi binder."

TABLE 4

Phosphorus binding by magnesium acetate (Data in this Table are taken from Table 3, page 399 of the Fine et al. publication cited above.)

| Expt. No. & mEq Magnesium Acetate (MgAc) | Calcium intake (mEq) | Fractional calcium absorption (%) | 10-h urinary calcium excretion (mEq) | Phosphorus intake (mmol) | Net phosphorus absorption (mmol) | Fractional phosphorus absorption[§] (%) |
| --- | --- | --- | --- | --- | --- | --- |
| 1. Standard Meal + Placebo | 15.4 ± 0.1 | 29.9 ± 2.9 | 3.0 ± 0.5 | 13.3 ± 0.1 | 9.7 ± 0.4 | 72.5 ± 2.9 |
| 2. Standard Meal + 10.2 mEq MgAc | 15.5 ± 0.1 | 25.9 ± 2.9 | 3.1 ± 0.6 | 13.4 ± 0.1 | 7.5 ± 0.4[§] | 55.8 ± 2.8[§] |

TABLE 4-continued

Phosphorus binding by magnesium acetate (Data in this Table are taken from
Table 3, page 399 of the Fine et al. publication cited above.)

| Expt. No. & mEq Magnesium Acetate (MgAc) | Calcium intake (mEq) | Fractional calcium absorption (%) | 10-h urinary calcium excretion (mEq) | Phosphorus intake (mmol) | Net phosphorus absorption (mmol) | Fractional phosphorus absorption[§] (%) |
|---|---|---|---|---|---|---|
| 3. Standard Meal + 19.4 mEq MgAc | 15.4 ± 0.1 | 24.5 ± 3.7 | 3.3 ± 0.6 | 13.3 ± 0.1 | 6.3 ± 0.5[§] | 47.1 ± 3.4[§] |
| 4. Standard Meal + 39.0 mEq MgAc | 15.4 ± 0.1 | 25.4 ± 3.8 | 3.9 ± 0.5 | 13.2 ± 0.1 | 4.8 ± 0.7[‖] | 37.0 ± 5.4[‖] |
| 5. Standard Meal + 77.2 mEq MgAc | 15.4 ± 0.1 | 24.0 ± 4.2 | 4.9 ± 0.5 | 13.3 ± 0.1 | 3.8 ± 0.6[¶] | 28.1 ± 4.8[¶] |
| 8. Fast | 0 | — | 1.5 ± 0.3 | 0 | — | — |

Results from eight subjects expressed as mean ± SE.
[§]Significantly lower than Experiment 1 ($P \leq 0.01$).
[‖]Significantly lower than Experiments 1 and 2 ($P \leq 0.003$).
[¶]Significantly lower than Experiments 1, 2, and 3 ($P \leq 0.004$).

As the data in Table 4 show, a magnesium salt such as magnesium acetate is a phosphate binder when ingested by humans, and the percentage of phosphate that is absorbed from the gastrointestinal tract decreases as the number of milliequivalents of the magnesium salt increase. The inventor believes that completion of a similar study using a magnesium dithiolane carboxylate salt as the magnesium salt will show that the magnesium dithiolane carboxylate salt is a phosphate binder. In other words, as the number of milliequivalents of a magnesium dithiolane carboxylate that are ingested with a standard meal is increased, the percentage of phosphate that is absorbed from the gastrointestinal tract will decrease from about 70% when no magnesium dithiolane carboxylate salt is added to the meal to about 20-30% when about 80 mEq of the magnesium dithiolane carboxylate salt are added to the standard meal.

EXAMPLE 4

Pharmacokinetics of Alpha-Lipoic Acid in Subjects with Severe Kidney Damage and End-stage Renal Disease. This safety study was reported by J. Teichert, T. Tuemmers, H. Achenbach, C. Preiss, R. Hermann, P. Ruus, and R. Preiss in J. Clin. Pharmacol. 2005, vol. 45, pages 313-328. In an open-label, parallel-group study involving 16 patients (8 with severely reduced renal function, 8 with end-stage renal disease (ESRD) needing hemodialysis), the effect of renal function on the pharmacokinetics, metabolism, and safety of alpha-lipoic acid (thioctic acid) was evaluated by comparing the pharmacokinetic parameters with those of a reference group of 8 healthy subjects.

After a predose blood sample had been taken, alpha-lipoic acid 600 mg was administered orally with 150 mL of water once daily for 4 days. Pharmacokinetic parameters were measured on study days 1 and 4 and before dosing on study days 2 and 3. The ESRD patients were investigated during the dialysis (day 1) and in the dialysis-free interval (day 4). They received a single oral dose of lipoic acid 600 mg in tablet form only on these two days. Meals were served at 4, 8, and 12 hours after drug administration. Prestudy examination and investigations included a medical history, physical examination, demographic data, vital signs, and electrocardiogram evaluations. Poststudy laboratory analyses (hematology, clinical chemistry, and urinalysis) were routinely performed, along with measurements of vital signs, ECG, and physical examinations. Renal status was confirmed by a 24-hour creatinine clearance determination at baseline (before dosing on day 1) and in the course of poststudy laboratory analyses (after dosing on day 4).

The investigators concluded that the pharmacokinetics of alpha-lipoic acid are not influenced by creatinine clearance and are unaffected in subjects with severely reduced kidney function or end-stage renal disease.

This study demonstrates that lipoic acid is safe when ingested by patients with kidney disease. The inventor believes that a study which is completed in the same manner as described above will show that a magnesium dithiolane carboxylate salt of the present invention will be safe when ingested by subjects with kidney disease. Further, the inventor believes that a study which is completed in the same manner as described above will show that a magnesium lipoate of the present invention will be safe when ingested by subjects with kidney disease.

The following example presents hypothetically useful therapeutic applications of representative pharmaceutical compositions of the present invention and their anticipated outcomes in treating hyperphosphatemia in subjects requiring such treatment. The examples are representative of the scope of the invention, and as such are not to be considered or construed as limiting the invention recited in the appended claims.

EXAMPLE 5

In Vivo Phosphorus Binding by Representative Compositions of the Present Invention. In vivo phosphorus binding by a composition of the present invention (a test composition) and a placebo will be assessed in 10 healthy human subjects. Each subject will be studied on three separate test days: fast, placebo, and a test composition. Five representative embodiments of compositions of the present invention (in other words, five test compositions) will be evaluated in independent studies: Embodiment 1 in which the test composition comprises a first quantity of calcium acetate and a second quantity of magnesium lipoate, wherein the combination of the first quantity and the second quantity equals a quantity of the composition that is therapeutically effective for binding phosphate in ingesta. Embodiment 2 in which the test composition comprises a first quantity of calcium succinate and a second quantity of magnesium lipoate, wherein the combination of the first quantity and the second quantity equals a quantity of the composition that is therapeutically effective for binding phosphate in ingesta. Embodiment 3 in which the test composition comprises a first quantity of lanthanum carbonate and a second quantity of magnesium lipoate, wherein the combination of the first quantity and the second quantity equals a quantity of the composition that is therapeutically effective for binding phosphate in ingesta. Embodiment 4 in which the test composition comprises a first quantity of sevelamer hydrochloride and a second quantity of magnesium lipoate, wherein the combination of the first quantity and the second quantity equals a quantity of the composition that is therapeutically effective for binding phosphate in ingesta. Embodiment 5 in which the test composition comprises a first quantity of the cationic polymer known as RenaGel® and a second quantity of magnesium lipoate, wherein the combination of the first quantity and the second quantity equals a quantity of the composition that is therapeutically effective for binding phosphate in ingesta.

On each day, subjects will be prepared by a mannitol-electrolyte gastrointestinal lavage, in order to cleanse the gastrointestinal tract. Four hours after completion of the washout, subjects will consume 25 mEq of the test composition or a placebo (lactose) with 100 mL of deionized water. On one of the test days (the fast day), subjects will ingest no meal, placebo or the test composition; the rest of the procedure will be the same. Then each subject will eat a test meal of 80 g ground sirloin steak, 100 g French fried potatoes, 30 g Swiss cheese and 250 mL water containing 10 g of polyethylene glycol (PEG3500) as a non-absorbable marker. After the meal, each subject will consume 25 mEq of the test composition, in the same form as will have been consumed prior to the meal, or additional placebo, with 100 mL of water. Duplicate meals will be prepared (one for consumption and one to be analyzed for phosphorus). The duplicate meals will be analyzed for phosphorus and are expected to contain about 350 mg of phosphorus.

Each test composition will be administered in gelatin capsules that contain the test composition. The total dose will equal 50 mEq of the test composition, one half of the dose (25 mEq) taken just before the meal and the other half immediately after the meal. On one test day a placebo will be taken instead of the test composition. The order of testing will be randomized.

Ten hours after a meal, a second lavage will be begun, using the procedure described above. This will remove unabsorbed material from the gut. All urine voided during the 10-hour period will be collected and analyzed for phosphorus. Rectal effluent will be collected, pooled with any stool passed during the 10-hour period and analyzed for phosphorus. Absorption will be calculated according to the following equation:

Net phosphorus ($P$) absorption=($P$ content of duplicate meal, mg)−(Total Effluent $P$, mg)

The results are expected to demonstrate that each test composition results in the inhibition of phosphorus absorption, when ingested close in time to food and beverage consumption. In other words, it is anticipated that on the placebo day, as much as about 70% or more of the dietary phosphorus will be absorbed from the GI tract of each subject. By comparison, on the day in which a test composition is ingested close in time to food and beverage consumption, it is anticipated that as little as about 20% of dietary phosphorus will be absorbed.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

I claim:

1. A composition comprising a cationic phosphate binder and a dithiolane carboxylate salt, wherein the cationic phosphate binder is selected from the group consisting of calcium acetate, calcium carbonate, calcium citrate, calcium alginate, calcium gluconate, calcium lactate, calcium sulfate, and calcium succinate, combinations of said calcium salts, lanthanum acetate, lanthanum carbonate, lanthanum hydroxide, lanthanum sulfate, and sevelamer, and wherein the dithiolane carboxylate salt has the structure

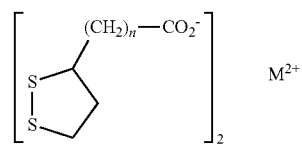

wherein M is magnesium and n is 4.

2. A composition comprising a cationic phosphate binder and a dithiolane carboxylate salt, wherein the cationic phosphate binder is a lanthanum salt selected from the group consisting of lanthanum carbonate, lanthanum hydroxide, and combinations thereof and the dithiolane carboxylate salt is magnesium lipoate.

3. A method for inhibiting absorption of dietary phosphorus from the alimentary tract of a mammal comprising orally ingesting a composition comprising a cationic phosphate binder and a dithiolane carboxylate salt in sufficient dose to control, abate, ameliorate, or prevent hyperphosphatemia or its associated pathologies.

4. The method of claim 3 wherein oral administration is by ingestion with food or by ingestion close in time to the consumption of dietary phosphate-containing food or beverage by a mammal.

5. The method of claim 4 wherein administration of the composition of claim 1 is a food additive within the meaning of title 21 of the CFR (Code of Federal Regulations) or a drug within the meaning of title 21 of the CFR (Code of Federal Regulations).

6. A composition comprising a cationic phosphate binder and a dithiolane carboxylate salt, wherein the cationic phosphate binder is a calcium salt is selected from the group consisting of calcium acetate, calcium carbonate, calcium citrate, calcium alginate, calcium gluconate, calcium lactate, calcium sulfate, and calcium succinate, and combinations thereof, and the dithiolane carboxylate salt is magnesium lipoate and said calcium salt and said dithiolane carboxylic acid salt are administered orally in a ratio of about 6:0.1 to about 1:6 by molar weight.

7. A composition for comprising a cationic phosphate binder and a dithiolane carboxylate salt, wherein the cationic phosphate binder is a water insoluble, cross-linked cationic polymer selected from the group consisting of a polyallylamine homopolymer, wherein said polyallylamine homopolymer comprises a repeat unit represented by the structural formula

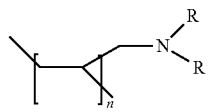

or a copolymer thereof, wherein n is an integer, and each R, independently, is H, an unsubstituted alkyl, alkylamino, or aryl group, or a substituted alkyl, alkylamino or aryl group, wherein the substituents are selected from the group consisting of quaternary ammonium, amino, hydroxyl, alkyoxy, carboxamide, sulfonamide, halogen, alkyl, aryl, hydrazine, guanidine, urea, and carboxylic acid ester, or a combination thereof; and a polymer characterized by a repeat unit having the formula

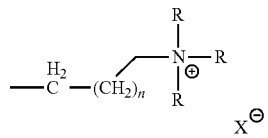

or a copolymer thereof, wherein each n is an integer, each R, independently, is H or a lower alkyl, alkylamino, or aryl group, and each $X^-$ is a carbonate or bicarbonate anion, and wherein the dithiolane carboxylate salt has the structure

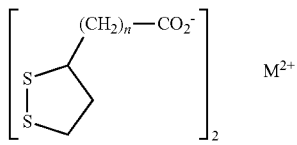

wherein M is magnesium and n is 4.

* * * * *